(12) United States Patent
Deligianni et al.

(10) Patent No.: US 10,065,658 B2
(45) Date of Patent: Sep. 4, 2018

(54) BIAS OF PHYSICAL CONTROLLERS IN A SYSTEM

(71) Applicant: International Business Machines Corporation, Armonk, NY (US)

(72) Inventors: Hariklia Deligianni, Alpine, NJ (US); Clifford A. Pickover, Yorktown Heights, NY (US); Anca Sailer, Scarsdale, NY (US)

(73) Assignee: International Business Machines Corporation, Armonk, NY (US)

( * ) Notice: Subject to any disclaimer, the term of this patent is extended or adjusted under 35 U.S.C. 154(b) by 0 days.

(21) Appl. No.: 15/161,649

(22) Filed: May 23, 2016

(65) Prior Publication Data

US 2017/0334456 A1    Nov. 23, 2017

(51) Int. Cl.
| | |
|---|---|
| *B60W 50/00* | (2006.01) |
| *B60W 50/08* | (2012.01) |
| *G05D 1/00* | (2006.01) |
| *A61B 5/18* | (2006.01) |
| *A61B 5/16* | (2006.01) |

(52) U.S. Cl.
CPC ........... *B60W 50/087* (2013.01); *A61B 5/165* (2013.01); *A61B 5/18* (2013.01); *G05D 1/0088* (2013.01); *B60W 2050/0071* (2013.01); *B60W 2420/42* (2013.01); *B60W 2540/22* (2013.01); *B60W 2540/26* (2013.01); *B60W 2750/40* (2013.01)

(58) Field of Classification Search
USPC .................................................... 701/36–49
See application file for complete search history.

(56) References Cited

U.S. PATENT DOCUMENTS

| | | | | |
|---|---|---|---|---|
| 5,798,695 A | * | 8/1998 | Metalis ................. | G08B 21/06 340/439 |
| 6,185,534 B1 | * | 2/2001 | Breese .................. | G10L 17/26 704/270 |

(Continued)

FOREIGN PATENT DOCUMENTS

| | | |
|---|---|---|
| EP | 2743117 A1 | 6/2014 |
| WO | 2010106217 A1 | 9/2010 |

OTHER PUBLICATIONS

Wikipedia, "Dead Man's switch", Wikipedia, the free encyclopedia, (2015).

(Continued)

*Primary Examiner* — Jonathan L Sample
(74) *Attorney, Agent, or Firm* — Cahn & Samuels, LLP (57) ABSTRACT

An embodiment of the invention provides a method to control a mechanical system based on the cognitive state of a user, where a first action is performed at an input device that is associated with the user. The cognitive state of the user is detected at the input device; and, a change to the first action is determined based on the cognitive state of the user. A controlled action is performed based on the recommended change. A system can include an input device associated with user, where a first action is performed at the input device. A processor connected to the input device detects the cognitive state of the user at the input device and determines a change to the first action based on the cognitive state of the user. A controller connected to the processor performs a controlled action based on the recommended change.

18 Claims, 5 Drawing Sheets

(56) References Cited

U.S. PATENT DOCUMENTS

| | | | | |
|---|---|---|---|---|
| 7,227,472 | B1* | 6/2007 | Roe | B60K 28/06 |
| | | | | 180/272 |
| 7,279,806 | B2* | 10/2007 | Hale | B60R 25/2009 |
| | | | | 307/10.4 |
| 7,940,914 | B2* | 5/2011 | Petrushin | G10L 17/26 |
| | | | | 379/265.06 |
| 8,630,768 | B2* | 1/2014 | McClellan | G01S 5/0027 |
| | | | | 701/36 |
| 8,775,186 | B2* | 7/2014 | Shin | G10L 17/26 |
| | | | | 455/414.1 |
| 9,636,064 | B2* | 5/2017 | Perugupalli | A61B 5/18 |
| 9,637,120 | B2* | 5/2017 | Laur | B60W 30/09 |
| 9,638,537 | B2* | 5/2017 | Abramson | G01C 21/3626 |
| 9,667,742 | B2* | 5/2017 | Weng | H04L 67/32 |
| 9,834,224 | B2* | 12/2017 | Gordon | B60W 50/082 |
| 2004/0036601 | A1* | 2/2004 | Obradovich | B60C 23/04 |
| | | | | 340/540 |
| 2006/0267781 | A1* | 11/2006 | Coulter | B60K 28/066 |
| | | | | 340/573.7 |
| 2007/0000374 | A1* | 1/2007 | Clark | G10H 1/0008 |
| | | | | 84/724 |
| 2009/0089709 | A1* | 4/2009 | Baier | G05B 19/409 |
| | | | | 715/817 |
| 2010/0070500 | A1* | 3/2010 | Cui | G06F 17/30557 |
| | | | | 707/736 |
| 2013/0110349 | A1* | 5/2013 | Tseng | B60W 50/087 |
| | | | | 701/36 |
| 2013/0231800 | A1* | 9/2013 | Ricci | G06F 9/54 |
| | | | | 701/1 |
| 2013/0325202 | A1* | 12/2013 | Howard | B60W 30/08 |
| | | | | 701/1 |
| 2014/0019522 | A1* | 1/2014 | Weng | G06F 17/30964 |
| | | | | 709/203 |
| 2014/0154659 | A1* | 6/2014 | Otwell | G09B 5/02 |
| | | | | 434/365 |
| 2014/0306833 | A1* | 10/2014 | Ricci | B60Q 1/00 |
| | | | | 340/901 |
| 2014/0309789 | A1* | 10/2014 | Ricci | B60Q 1/00 |
| | | | | 700/276 |
| 2014/0309813 | A1* | 10/2014 | Ricci | B60Q 1/00 |
| | | | | 701/2 |
| 2014/0309863 | A1* | 10/2014 | Ricci | G01C 21/3484 |
| | | | | 701/36 |
| 2014/0309864 | A1* | 10/2014 | Ricci | H04W 48/04 |
| | | | | 701/36 |
| 2014/0365062 | A1* | 12/2014 | Urhahne | B60W 50/16 |
| | | | | 701/23 |
| 2015/0120081 | A1* | 4/2015 | Forcke | B60W 40/08 |
| | | | | 701/1 |
| 2015/0221247 | A1* | 8/2015 | Herger | G02B 27/017 |
| | | | | 345/8 |
| 2015/0224998 | A1* | 8/2015 | Prakah-Asante | B60W 50/12 |
| | | | | 701/36 |
| 2015/0326570 | A1* | 11/2015 | Publicover | G06F 21/64 |
| | | | | 726/4 |
| 2015/0371465 | A1* | 12/2015 | Garrett | G07C 5/008 |
| | | | | 701/29.1 |
| 2016/0001781 | A1* | 1/2016 | Fung | G06F 19/345 |
| | | | | 701/36 |
| 2016/0008632 | A1* | 1/2016 | Wetmore | A61N 7/00 |
| | | | | 601/2 |
| 2016/0106355 | A1* | 4/2016 | Perugupalli | G06K 9/0061 |
| | | | | 351/210 |
| 2016/0221502 | A1* | 8/2016 | Gordon | B60R 1/00 |
| 2016/0293024 | A1* | 10/2016 | Kozloski | G06Q 10/109 |
| 2016/0318468 | A1* | 11/2016 | Ricci | B60R 16/037 |
| 2016/0375900 | A1* | 12/2016 | Laur | B60W 30/09 |
| | | | | 701/41 |
| 2017/0021279 | A1* | 1/2017 | Kim | A63F 13/00 |
| 2017/0106876 | A1* | 4/2017 | Gordon | B60W 50/082 |
| 2017/0160891 | A1* | 6/2017 | Chefalas | G06F 3/0484 |
| 2017/0168703 | A1* | 6/2017 | Feris | G06F 3/04855 |
| 2017/0195514 | A1* | 7/2017 | Goldberg | H04N 1/32128 |

OTHER PUBLICATIONS

Taylor, "Technologies for supporting human cognitive control." Human Factors in the 21st Century (2002).

Lam et al., "A POMDP framework for human-in-the-loop system." Decision and Control (CDC), 2014 IEEE 53rd Annual Conference on. IEEE, 2014.

Arunkumar et al., "Monitioring Driver Alertness and Avoiding Traffic Collision Using WSN." International Journal of Computer Science and Mobile Computing (2013).

Maiti et al., "An innovative prototype to prevent accidents using eye blink sensors and accelerometer ADXL330." Computing and Communication (IEMCON), 2015 International Conference and Workshop on IEEE, 2015.

The Atlantic; "This App Reads Your Emotions on Your Face" [retrieved on Apr. 27, 2016]. Retrieved from the Internet: <URL: http://www.theatlantic.com/technology/archive/2014/01/this-app-reads-your-emotions-on-your-face/282993/>.

Dark Daily; "Cheap, Disposable Biometric Patch to Monitor Stress and Fatigue in Military Personnel May Be Adapted to Monitor Biomarkers Used by Clinical Pathology Laboratories" [retrieved on Apr. 27, 2016]. Retrieved from the Internet: <URL: http://www.darkdaily.com/cheap-disposable-biometric-patch-to-monitor-stress-and-fatigue-in-military-personnel-may-be-adapted-to-monitor-biomarkers-used-by-clinical-pathology-laboratories-1210#axzz472FYRXxs>.

Technology Review; "Wrist Sensor Tells You How Stressed Out You Are" [retrieved on Apr. 27, 2016]. Retrieved from the Internet: <URL: https://www.technologyreview.com/s/508716/wrist-sensor-tells-you-how-stressed-out-you-are>.

Motor Authority; "Ford Developing Biometric Driver Stress Detectors to Improve Safety" [retrieved on Apr. 27, 2016]. Retrieved from the Internet: <URL: http://www.motorauthority.com/news/1077304_ford-developing-biometric-driver-stress-detectors-to-improve-safety>.

Research Gate; "Biometric study using hyperspectral imaging during stress" [retrieved on Apr. 27, 2016]. Retrieved from the Internet: <URL: https://www.researchgate.net/publication/258449278_Biometric_study_using_hyperspectral_imaging_during_stress>.

* cited by examiner

BIAS OF PHYSICAL CONTROLLERS IN A SYSTEM

BACKGROUND

The present invention relates to systems, methods, and computer program products for bias of physical controllers in a system. As used herein, the term "mechanical systems" includes industrial or factory machines and vehicles, such as, for example, automobiles, trains, boats, airplanes, drones, etc. The physical controllers can include, for example, wheels, levers, pedals, joysticks, etc. Physical controllers control the movements of the mechanical systems. For example, levers can control the robotic arm of a factory machine. In another example, the wheel of a boat controls the rudder and therefore the steering of the vessel.

SUMMARY OF THE INVENTION

An embodiment of the invention provides a method to control a mechanical system based on the cognitive state of a user, where a first action is performed at an input device that is associated with the user. The cognitive state of the user is detected at the input device; and, a change to the first action is determined based on the cognitive state of the user. A controlled action is performed based on the recommended change.

In a least one embodiment of the invention, a system to control a mechanical system based on the cognitive state of a user includes an input device associated with user, where a first action is performed at the input device. A processor connected to the input device detects the cognitive state of the user at the input device and determines a change to the first action based on the cognitive state of the user. A controller connected to the processor performs a controlled action based on the recommended change.

In another embodiment of the invention, an input device associated with user includes a user interface, where a first action is performed at the user interface. A first processing unit connected to the user interface detects the cognitive state of the user at the user interface. A second processing unit connected to the first processing unit determines a change to a first action based on the cognitive state of the user.

BRIEF DESCRIPTION OF THE SEVERAL VIEWS OF THE DRAWINGS

The present invention is described with reference to the accompanying drawings. In the drawings, like reference numbers indicate identical or functionally similar elements.

DETAILED DESCRIPTION

Exemplary, non-limiting, embodiments of the present invention are discussed in detail below. While specific configurations are discussed to provide a clear understanding, it should be understood that the disclosed configurations are provided for illustration purposes only. A person of ordinary skill in the art will recognize that other configurations may be used without departing from the spirit and scope of the invention.

At least one embodiment of the invention provides a system including a mechanical or transportation device and a means for determining an emotional state of a user of a physical controller of the device, such as a joystick, a wheel, a lever, an vehicle pedal, an airplane control lever, drone controllers, a factory machine switch, a touch screen display, etc. Based on the user's emotional state and/or the controller use, the system can take a controlled action and/or offer advice (e.g., with respect to the selection and/or movement of the physical controller). Fatigue level of the user can be estimated, for example, from an electronic calendar for the user. The estimated fatigue level as well as information on medications and medication schedules associated with the user can affect, or bias, the physical device controller response.

The system in at least one embodiment is applied to any physical controller. For example, the system can be applied to airplanes in which cockpit flight controls may include a control yoke (also known as a control column), rudder pedals, and throttle controls to control engine speed or thrust for powered aircraft. An autopilot system can be employed, which can control the trajectory of a vehicle without constant hands-on control by a human operator being required.

The controlled action may include a change from the normal action, invocation of autopilot, delay of the action, a parallel signal sent to a third party (e.g., ground control), and/or an offering of advice with respect to the action. Physical features of the device controller may change, such as force feedback, vibration, and responsiveness to force, and/or the inclusions of detents.

The emotional state of the user can include a measure of anxiety, elation, hesitance, distraction level, and/or fatigue level. The fatigue level can be estimated from an electronic calendar associated with the user (e.g., the schedule of a pilot, car driver, etc.). The emotional state can be measured in real time with a biometric monitor and/or with a sensor in the controller that measures the amount of pressure applied to the controller by the user. This information may be compared against security outcomes of similar actions, performed by similar users, presenting a similar measure of the emotional state.

Biomonitors can include systems for monitoring and analyzing facial expressions, including facial changes in response to a person's internal emotional states, intentions, or social communications. Facial expression monitoring and analysis can include measurement of facial motion and recognition of expression with a certain degree of confidence. Such facial expression systems may make use of a processing stage to automatically find the face region for input images or videos. In facial feature extraction, a number of methods may be used, including geometric feature-based methods and appearance-based methods. In some cases, the facial components may form a feature vector that represents the face geometry. The system may also consider transitions among expressions and possible eliciting condition.

Other biomonitors can include a disposable biometric patch to monitor stress and fatigue, for example, by monitoring chemicals in sweat that are indicators of stress and fatigue. Such biometric patches can also be employed on wearable devices (e.g., bracelet, glasses) or on the physical controller (e.g., grip portion of a lever). The biomonitor can measure proxies for excitement or stress, including increased motion, increased skin conductance from perspiration, and/or elevated skin temperature. The system can integrate various biometric measurements such as pulse, galvanic skin response, and/or breathing rate to determine a user's "workload", a concept that relates to attention and performance while operating a device. This functionality may be in the physical controller or in the seat of a user.

In at least one embodiment, the biomonitor can use hyperspectral imaging to identify stress. Transient stress can result in a variety of physiological changes that can be seen in the face. Although the conditions can be seen visibly, the conditions can affect the emissivity and absorption properties of the skin, which imaging spectrometers (e.g., Hyperspectral (HS) cameras) can quantify at every image pixel. Other biomonitors can include devices that monitor the user's use of a physical controller and detect patterns of potential problems that may be correlated with states such as fatigue, distraction, elation, suicide, etc. For example, the biomonitor can detect a pedal, lever, wheel, or other physical controller that the user moves in a wild manner, swings haphazardly, shakes, or squeezes too tightly or loosely.

Features that can be used to determine the user's emotional state may include acoustic features, voice prosody, shaking of the hand on the controller, visual features, linguistic features, and physical features that are extracted from signals obtained by one or more sensors with a processor. The acoustic, visual, linguistic, and physical features may be analyzed with one or more machine learning algorithms and an emotional state of a user may be extracted from analysis of the features. Various features may be extracted from signals obtained by one or more sensors embedded on, for example, an analog processor.

In some cases, the system may estimate an emotional state, identify nervousness, panic, anger, conditions matching mental illness (e.g., epilepsy), etc., wherein machine learning may be used to correlate monitored data to emotional conditions. In at least one embodiment, the system includes a cognitive controller and switch to estimate the condition of the person operating the apparatus and move from manual operation of the apparatus to autopilot or other channels of operations (e.g., ground control in case of an airplane). A controlled action can include limiting operational functionality, such as electronically or mechanically limiting the gas acceleration pedal on an automobile.

Calendar input can be used to estimate the user's fatigue level. For example, a pilot's calendar may indicate his accumulated hours of flight or the fact that he just completed a flight and did not sleep). Furthermore, the calendar input may include medications currently taken by the user, along with the medication dosage and timing.

Bias of a physical device controller may be changed based on impairments, such as intoxication, physical impairment, medical impairment, and/or emotional impairment. The system may function as an impaired operator detection system for detecting impairment of an operator of any equipment, system, or vehicle which requires continuous compensatory tracking, or nulling, of course deviation error. For example, ground control operators are notified when a pilot is impaired (e.g., distracted, drowsy, intoxicated). The pilot can also be notified of the impairment and data relating to vehicle operator impairment can be logged for further analysis.

The system can monitor the vehicle operator, the environment ahead of the vehicle, and/or forces acting on the vehicle using optical sensors and/or accelerometers. For example, an optical sensor monitors the vehicle (e.g., plane, car, train) operator to detect eye blinks, head nods, head rotations, and/or gaze fixation. Another optical sensor cab monitor the road ahead of the vehicle to detect lane deviation, lane centering, and/or time to collision. The accelerometers may detect acceleration in the direction of vehicle travel and/or lateral acceleration.

In at least one embodiment, information on medicines taken by the vehicle operator influences physical responsiveness of the joystick (e.g., speed of response, damping of vibrations, force feedback, force needed to move the joystick, thresholds, needed to be exceeded before ground control, family member, or autopilot is alerted).

Figure 1:
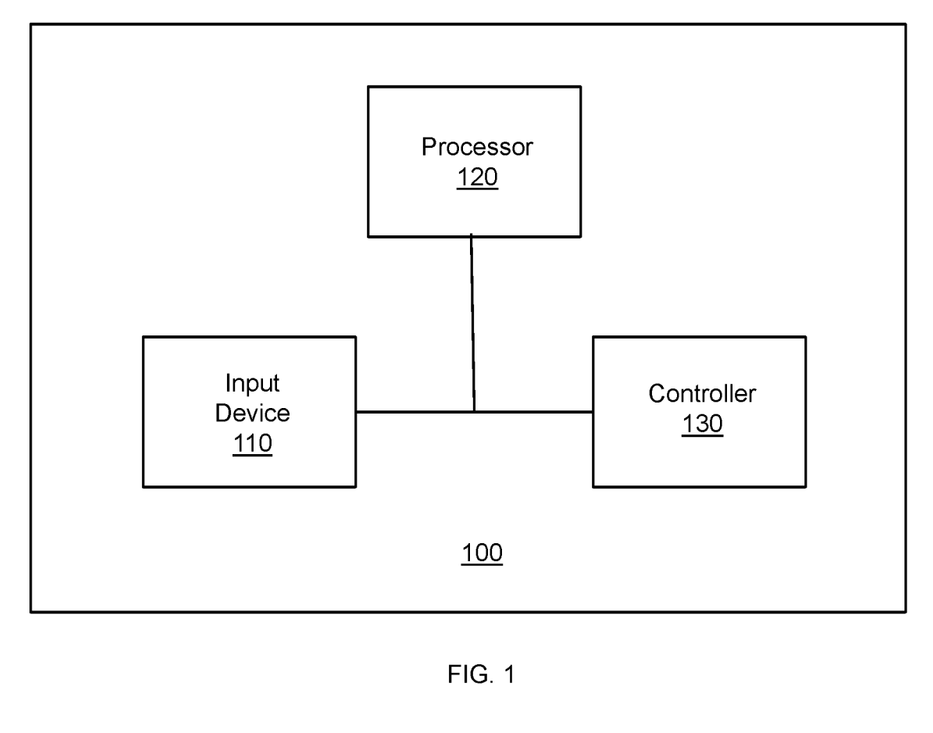
FIG. 1 is a diagram illustrating a system for bias of physical controllers in mechanical systems according to an embodiment of the invention.
Figure 2:
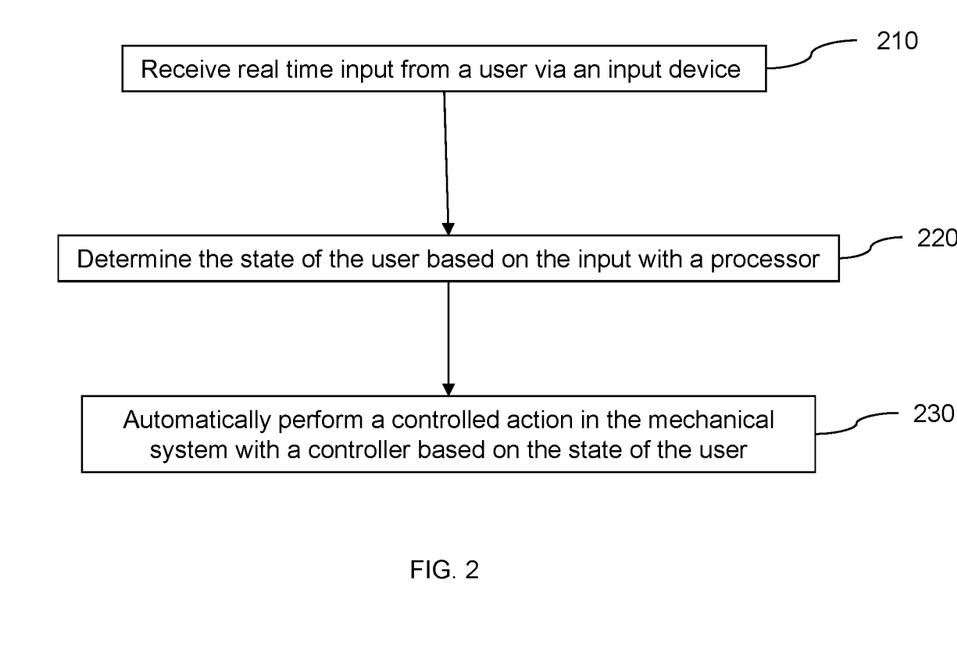
FIG. 2 is a flow diagram illustrating a method for bias of physical controllers in mechanical systems according to an embodiment of the invention.

FIG. 1 is a diagram illustrating a system 100 for bias of physical controllers in mechanical systems according to an embodiment of the invention. FIG. 2 is a flow diagram illustrating a method for bias of physical controllers in mechanical systems according to an embodiment of the invention (e.g., using the system 100). The system 100 can include an input device 110 that receives real time input from a user (210), such as, for example, a facial expression and/or audible input. As used herein the term "input device" includes a computer hardware device for receiving input from a user, such as, for example, a camera, a microphone, a keyboard, a mouse, and/or an internet or cable port, etc.

The system 100 can also include a processor 120 that determines the state of the user based on the input (220). As used herein the term "processor" includes a computer hardware device connected to the input device 110, such as, for example, a CPU, integrated circuit, or microprocessor. As used herein, the term "connected" includes operationally connected, logically connected, in communication with, physically or wirelessly connected, engaged, coupled, contacts, linked, affixed, and attached.

In at least one embodiment, the state of the user includes above a threshold level of anxiety, above a threshold level of level of elation, above a threshold level hesitation, above a threshold level of distraction, above a threshold level of fatigue, above a threshold level of frustration, above a threshold level of nervousness, above a threshold level of panic, above a threshold level of anger, below a threshold level of expertise, and/or a disease state (e.g., Parkinson's disease). The processor 120 can determine the state of the user from camera input (e.g., a facial expression of the user, gaze fixation by the user), information from a calendar of the user, a profile of the user, and/or analysis of audible input from the microphone. The profile of the user can include the level of expertise of the user, the disease state of the user, and/or a list of medications of the user. The list of medications of the user may also be obtained from an online database, a web crawler, or from manual input by the user.

If the user is taking a medication with a soporific affect, like some antihistamines, a likely state may be fatigue or tiredness. A user may tell a device that he or she has taken an antihistamine, and thus a physical controller may vibrate with greater intensity to suggest a possible deviation from expected behavior based on this information. A physical controller may change its sensitivity to resist motions that are closer to a danger zone of use.

The audible input can be analyzed for the detection of keywords, tone of spoken words, frequency of the spoken words, and pitch of the spoken words. For example, the processor 120 can determine that the user's state is above a threshold level of fatigue when the processor 120 identifies that the user has spoken the keywords "tired" and "sleepy" more than a threshold number of times in a fixed time duration. In another example, the processor 120 can determine that the user's state is above a threshold level of anxiety when the processor 120 words spoken by the user are within a predetermined tonal range, a predetermined frequency range, and/or a predetermined pitch range.

The processor 120 can determine that the user's state is above a threshold level of fatigue based on the calendar of the user (e.g., ratio of work hours (meetings, appointments, driving time, flying time) to non-work hours in a predefined period, amount of sleep in a predefined period), a facial expression of the user, and head nods detected by the input device. In at least one embodiment, the mechanical system is an automobile and the input device is a camera on the automobile, where the processor 120 determines that the user is distracted and/or fatigued when lane deviation is detected in the input.

In addition, the processor 120 can determine that the user's state is above a threshold level of hesitation by a timing analysis, where the timing analysis can include determining an average response time for a task by the user, determining a current response time for the task by the user, and determining that the user is above a threshold level of hesitation when the current response time for the task by the user exceeds the average response time for a task by the user by a threshold amount of time. The processor 120 can determine that the user's state is above a threshold level of anxiety by detecting the presence of hand tremors of the user with a sensor in the physical controller of the mechanical system. As used herein, the term "physical controller" includes a mechanical device for receiving user commands to control the mechanical system, such as, for example, a wheel, a lever, a joystick, a pedal, a switch, etc. Physical controllers can be designed to directly interface with the user's hands or feet.

Based on this disclosure, one of ordinary skill in the art should appreciate that different mixtures of the above-described thresholds may be used in a particular embodiment.

As used herein, the term "controller" includes a computer hardware device connected to the processor 120. The system 100 can include a controller 130 for automatically performing a controlled action in the mechanical system (i.e., the controlled action is performed without manual user input) based on the state of the user (230). In at least one embodiment, the controlled action is only performed when the user is determined to have or satisfy a threshold number (e.g., 3) of states that trigger a controlled action within a predefined time period (e.g., it is determined that the user is fatigued, anxious, and frustrated in a period of 5 minutes).

The controlled action can include activating an autopilot system in the mechanical system when the processor 120 determines that the state of the user is above a threshold level of anxiety, above a threshold level of elation, above a threshold level of hesitation, above a threshold level of distraction, above a threshold level of fatigue, above a threshold level of frustration, above a threshold level of nervousness, above a threshold level of panic, above a threshold level of anger, below a threshold level of expertise, and/or a neurological disease state. For example, the processor 120 can suggest that the autopilot be engaged, and if the user does not respond appropriately within 10 seconds, autopilot will be engaged.

In another embodiment, the controlled action includes delaying a command from the user when the processor 120 determines that the state of the user is above a threshold level of anxiety, above a threshold level of elation, above a threshold level of hesitation, above a threshold level of distraction, above a threshold level of fatigue, above a threshold level of frustration, above a threshold level of nervousness, above a threshold level of panic, above a threshold level of anger, below a threshold level of expertise, and/or a neurological disease state. For example, when the processor 120 determines that the state of the user includes above a threshold level of panic, the action that is triggered by manual actuation of a switch is delayed for a predetermined amount of time if the delay does not impose a risk.

The controlled action can include sending an alert to a third party (e.g., ground control) indicating the determined state of the user when the processor 120 determines that the state of the user is above a threshold level of anxiety, above a threshold level of elation, above a threshold level of hesitation, above a threshold level of distraction, above a threshold level of fatigue, above a threshold level of frustration, above a threshold level of nervousness, above a threshold level of panic, above a threshold level of anger, below a threshold level of expertise, and/or a neurological disease state.

The controlled action can include providing a recommendation to the user (e.g., activate autopilot, lights, windshield wipers, and/or 4-wheel drive) when the processor 120 determines that the state of the user is above a threshold level of anxiety, above a threshold level of elation, above a threshold level of hesitation, above a threshold level of distraction, above a threshold level of fatigue, above a threshold level of frustration, above a threshold level of nervousness, above a threshold level of panic, above a threshold level of anger, below a threshold level of expertise, and/or a neurological disease state.

The controlled action can include increasing the sensitivity (responsiveness to force) of the physical controller of the mechanical system when the processor 120 determines that the state of the user is above a threshold level of anxiety, above a threshold level of elation, above a threshold level of hesitation, above a threshold level of distraction, above a threshold level of fatigue, above a threshold level of frustration, above a threshold level of nervousness, above a threshold level of panic, above a threshold level of anger, below a threshold level of expertise, and/or a neurological disease state.

The controlled action can include decreasing the sensitivity of the physical controller of the mechanical system when the processor 120 determines that the state of the user is above a threshold level of anxiety, above a threshold level of elation, above a threshold level of hesitation, above a threshold level of distraction, above a threshold level of fatigue, above a threshold level of frustration, above a threshold level of nervousness, above a threshold level of panic, above a threshold level of anger, below a threshold level of expertise, and/or a neurological disease state.

The controlled action can include increasing the amount of vibration feedback and/or the type of vibration feedback (e.g., sine wave, square wave, triangle wave, sawtooth wave, periodicity, frequency, amplitude, etc.) in the physical controller of the mechanical system when the processor 120 determines that the state of the user is above a threshold level of anxiety, above a threshold level of elation, above a threshold level of hesitation, above a threshold level of distraction, above a threshold level of fatigue, above a threshold level of frustration, above a threshold level of nervousness, above a threshold level of panic, above a threshold level of anger, below a threshold level of expertise, and/or a neurological disease state.

The controlled action can include decreasing the amount of vibration feedback and/or the type of vibration feedback in the physical controller of the mechanical system when the processor 120 determines that the state of the user is above a threshold level of anxiety, above a threshold level of elation, above a threshold level of hesitation, above a threshold level of distraction, above a threshold level of fatigue, above a threshold level of frustration, above a threshold level of nervousness, above a threshold level of panic, above a threshold level of anger, below a threshold level of expertise, and/or a neurological disease state.

The controlled action can include activation of a detent in the physical controller when the processor 120 determines that the state of the user is above a threshold level of anxiety, above a threshold level of elation, above a threshold level of hesitation, above a threshold level of distraction, above a threshold level of fatigue, above a threshold level of frustration, above a threshold level of nervousness, above a threshold level of panic, above a threshold level of anger, below a threshold level of expertise, and/or a neurological disease state. The spacing of detents along a range and the amount of detents may be modified. As with the vibrations, the detents may have a shape that changes. For example, as a user moves a physical controller from up, to down, to up, the user's hand feels different clicks. The square wave may produce a harsh feel. A sine wave detent may be smoother.

A state may be a deviation from a baseline for the user of a particular cohort. As used herein, the term "cohort" can include a group of people with similar characteristics, such as beginning drivers, people with early-stage Parkinson's, etc. For example, the system may have monitored a collection of people with early-stage Parkinson's as well as a particular user with this condition, and then detected a deviation that is beyond a threshold for a user and/or the cohort.

In at least one embodiment, bias of the physical device controller may be changed based on impairments, such as intoxication, physical impairment, medical impairment, or emotional impairment. This may function as an impaired operator detection system for detecting impairment of an operator of any equipment, system, or vehicle which requires continuous compensatory tracking, or nulling, of course deviation error.

In another embodiment of the invention, an input device associated with user includes a user interface, where a first action is performed at the user interface. The user interface (also referred to herein as a "physical controller") can control the movements of mechanical systems and can include, for example, a wheel, a lever, a pedal, or a joystick. A first processing unit connected to the user interface detects the cognitive state of the user at the user interface. As used herein the term "processing unit" includes a computer hardware device connected to the user interface, such as, for example, a CPU, integrated circuit, or microprocessor. A second processing unit connected to the first processing unit can determine a change to a first action based on the cognitive state of the user.

The present invention may be a system, a method, and/or a computer program product at any possible technical detail level of integration. The computer program product may include a computer readable storage medium (or media) having computer readable program instructions thereon for causing a processor to carry out aspects of the present invention.

The computer readable storage medium can be a tangible device that can retain and store instructions for use by an instruction execution device. The computer readable storage medium may be, for example, but is not limited to, an electronic storage device, a magnetic storage device, an optical storage device, an electromagnetic storage device, a semiconductor storage device, or any suitable combination of the foregoing. A non-exhaustive list of more specific examples of the computer readable storage medium includes the following: a portable computer diskette, a hard disk, a random access memory (RAM), a read-only memory (ROM), an erasable programmable read-only memory (EPROM or Flash memory), a static random access memory (SRAM), a portable compact disc read-only memory (CD-ROM), a digital versatile disk (DVD), a memory stick, a floppy disk, a mechanically encoded device such as punchcards or raised structures in a groove having instructions recorded thereon, and any suitable combination of the foregoing. A computer readable storage medium, as used herein, is not to be construed as being transitory signals per se, such as radio waves or other freely propagating electromagnetic waves, electromagnetic waves propagating through a waveguide or other transmission media (e.g., light pulses passing through a fiber-optic cable), or electrical signals transmitted through a wire.

Computer readable program instructions described herein can be downloaded to respective computing/processing devices from a computer readable storage medium or to an external computer or external storage device via a network, for example, the Internet, a local area network, a wide area network and/or a wireless network. The network may comprise copper transmission cables, optical transmission fibers, wireless transmission, routers, firewalls, switches, gateway computers and/or edge servers. A network adapter card or network interface in each computing/processing device receives computer readable program instructions from the network and forwards the computer readable program instructions for storage in a computer readable storage medium within the respective computing/processing device.

Computer readable program instructions for carrying out operations of the present invention may be assembler instructions, instruction-set-architecture (ISA) instructions, machine instructions, machine dependent instructions, microcode, firmware instructions, state-setting data, configuration data for integrated circuitry, or either source code or object code written in any combination of one or more programming languages, including an object oriented programming language such as Smalltalk, C++, or the like, and procedural programming languages, such as the "C" programming language or similar programming languages. The computer readable program instructions may execute entirely on the user's computer, partly on the user's computer, as a stand-alone software package, partly on the user's computer and partly on a remote computer or entirely on the remote computer or server. In the latter scenario, the remote computer may be connected to the user's computer through any type of network, including a local area network (LAN) or a wide area network (WAN), or the connection may be made to an external computer (for example, through the Internet using an Internet Service Provider). In some embodiments, electronic circuitry including, for example, programmable logic circuitry, field-programmable gate arrays (FPGA), or programmable logic arrays (PLA) may execute the computer readable program instructions by utilizing state information of the computer readable program instructions to personalize the electronic circuitry, in order to perform aspects of the present invention.

Aspects of the present invention are described herein with reference to flowchart illustrations and/or block diagrams of methods, apparatus (systems), and computer program products according to embodiments of the invention. It will be understood that each block of the flowchart illustrations and/or block diagrams, and combinations of blocks in the flowchart illustrations and/or block diagrams, can be implemented by computer readable program instructions.

These computer readable program instructions may be provided to a processor of a general purpose computer, special purpose computer, or other programmable data processing apparatus to produce a machine, such that the instructions, which execute via the processor of the computer or other programmable data processing apparatus, create means for implementing the functions/acts specified in the flowchart and/or block diagram block or blocks. These computer readable program instructions may also be stored in a computer readable storage medium that can direct a computer, a programmable data processing apparatus, and/or other devices to function in a particular manner, such that the computer readable storage medium having instructions stored therein comprises an article of manufacture including instructions which implement aspects of the function/act specified in the flowchart and/or block diagram block or blocks.

The computer readable program instructions may also be loaded onto a computer, other programmable data processing apparatus, or other device to cause a series of operational steps to be performed on the computer, other programmable apparatus or other device to produce a computer implemented process, such that the instructions which execute on the computer, other programmable apparatus, or other device implement the functions/acts specified in the flowchart and/or block diagram block or blocks.

The flowchart and block diagrams in the Figures illustrate the architecture, functionality, and operation of possible implementations of systems, methods, and computer program products according to various embodiments of the present invention. In this regard, each block in the flowchart or block diagrams may represent a module, segment, or portion of instructions, which comprises one or more executable instructions for implementing the specified logical function(s). In some alternative implementations, the functions noted in the blocks may occur out of the order noted in the Figures. For example, two blocks shown in succession may, in fact, be executed substantially concurrently, or the blocks may sometimes be executed in the reverse order, depending upon the functionality involved. It will also be noted that each block of the block diagrams and/or flowchart illustration, and combinations of blocks in the block diagrams and/or flowchart illustration, can be implemented by special purpose hardware-based systems that perform the specified functions or acts or carry out combinations of special purpose hardware and computer instructions.

Figure 3:
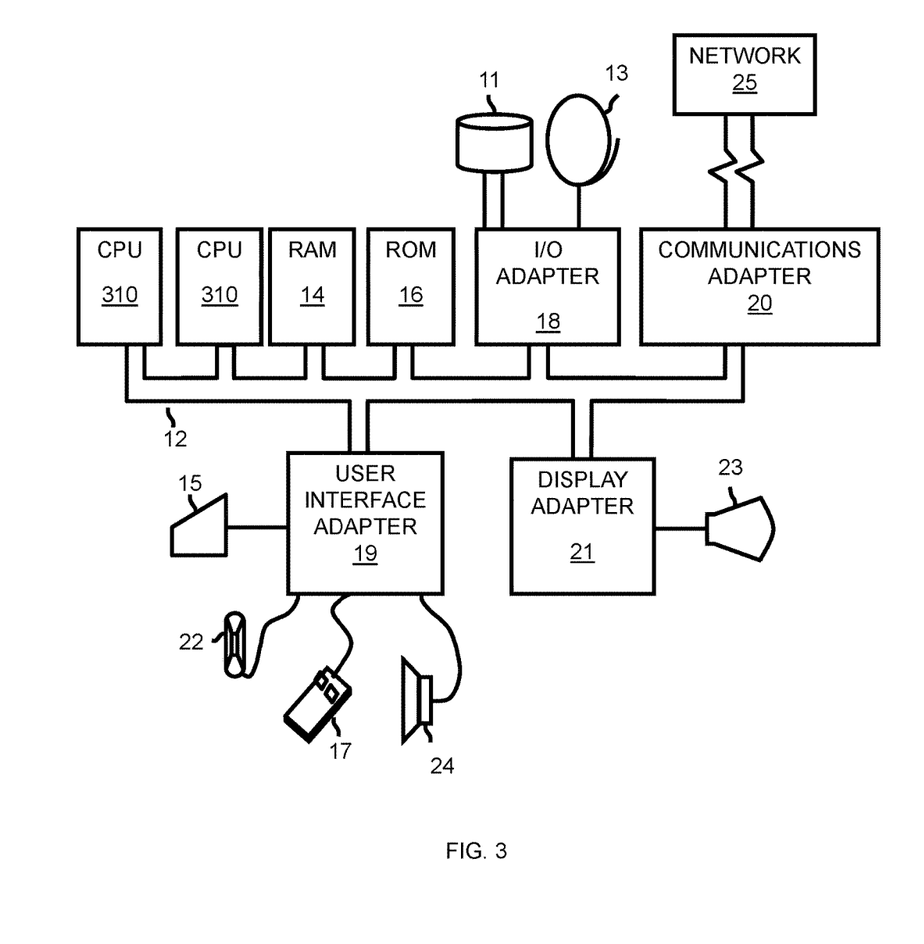
FIG. 3 is a diagram illustrating a computer program product for bias of physical controllers in mechanical systems according to an embodiment of the invention.

Referring now to FIG. 3, a representative hardware environment for practicing at least one embodiment of the invention is depicted. This schematic drawing illustrates a hardware configuration of an information handling/computer system in accordance with at least one embodiment of the invention. The system comprises at least one processor or central processing unit (CPU) 310. The CPUs 310 are interconnected with system bus 12 to various devices such as a random access memory (RAM) 14, read-only memory (ROM) 16, and an input/output (I/O) adapter 18. The I/O adapter 18 can connect to peripheral devices, such as disk units 11 and tape drives 13, or other program storage devices that are readable by the system. The system can read the inventive instructions on the program storage devices and follow these instructions to execute the methodology of at least one embodiment of the invention. The system further includes a user interface adapter 19 that connects a keyboard 15, mouse 17, speaker 24, microphone 22, and/or other user interface devices such as a touch screen device (not shown) to the bus 12 to gather user input. Additionally, a communication adapter 20 connects the bus 12 to a data processing network 25, and a display adapter 21 connects the bus 12 to a display device 23 which may be embodied as an output device such as a monitor, printer, or transmitter, for example.

It is to be understood that although this disclosure includes a detailed description on cloud computing, implementation of the teachings recited herein are not limited to a cloud computing environment. Rather, embodiments of the present invention are capable of being implemented in conjunction with any other type of computing environment now known or later developed.

Cloud computing is a model of service delivery for enabling convenient, on-demand network access to a shared pool of configurable computing resources (e.g., networks, network bandwidth, servers, processing, memory, storage, applications, virtual machines, and services) that can be rapidly provisioned and released with minimal management effort or interaction with a provider of the service. This cloud model may include at least five characteristics, at least three service models, and at least four deployment models.

Characteristics are as follows:

On-demand self-service: a cloud consumer can unilaterally provision computing capabilities, such as server time and network storage, as needed automatically without requiring human interaction with the service's provider.

Broad network access: capabilities are available over a network and accessed through standard mechanisms that promote use by heterogeneous thin or thick client platforms (e.g., mobile phones, laptops, and PDAs).

Resource pooling: the provider's computing resources are pooled to serve multiple consumers using a multi-tenant model, with different physical and virtual resources dynamically assigned and reassigned according to demand. There is a sense of location independence in that the consumer generally has no control or knowledge over the exact location of the provided resources but may be able to specify location at a higher level of abstraction (e.g., country, state, or datacenter).

Rapid elasticity: capabilities can be rapidly and elastically provisioned, in some cases automatically, to quickly scale out and rapidly released to quickly scale in. To the consumer, the capabilities available for provisioning often appear to be unlimited and can be purchased in any quantity at any time.

Measured service: cloud systems automatically control and optimize resource use by leveraging a metering capability at some level of abstraction appropriate to the type of service (e.g., storage, processing, bandwidth, and active user accounts). Resource usage can be monitored, controlled, and reported, providing transparency for both the provider and consumer of the utilized service.

Service Models are as follows:

Software as a Service (SaaS): the capability provided to the consumer is to use the provider's applications running on a cloud infrastructure. The applications are accessible from various client devices through a thin client interface such as a web browser (e.g., web-based e-mail). The consumer does not manage or control the underlying cloud infrastructure including network, servers, operating systems, storage, or even individual application capabilities, with the possible exception of limited user-specific application configuration settings.

Platform as a Service (PaaS): the capability provided to the consumer is to deploy onto the cloud infrastructure consumer-created or acquired applications created using programming languages and tools supported by the provider.

The consumer does not manage or control the underlying cloud infrastructure including networks, servers, operating systems, or storage, but has control over the deployed applications and possibly application hosting environment configurations.

Infrastructure as a Service (IaaS): the capability provided to the consumer is to provision processing, storage, networks, and other fundamental computing resources where the consumer is able to deploy and run arbitrary software, which can include operating systems and applications. The consumer does not manage or control the underlying cloud infrastructure but has control over operating systems, storage, deployed applications, and possibly limited control of select networking components (e.g., host firewalls).

Deployment Models are as follows:

Private cloud: the cloud infrastructure is operated solely for an organization. It may be managed by the organization or a third party and may exist on-premises or off-premises.

Community cloud: the cloud infrastructure is shared by several organizations and supports a specific community that has shared concerns (e.g., mission, security requirements, policy, and compliance considerations). It may be managed by the organizations or a third party and may exist on-premises or off-premises.

Public cloud: the cloud infrastructure is made available to the general public or a large industry group and is owned by an organization selling cloud services.

Hybrid cloud: the cloud infrastructure is a composition of two or more clouds (private, community, or public) that remain unique entities but are bound together by standardized or proprietary technology that enables data and application portability (e.g., cloud bursting for load-balancing between clouds).

A cloud computing environment is service oriented with a focus on statelessness, low coupling, modularity, and semantic interoperability. At the heart of cloud computing is an infrastructure that includes a network of interconnected nodes.

Figure 4:
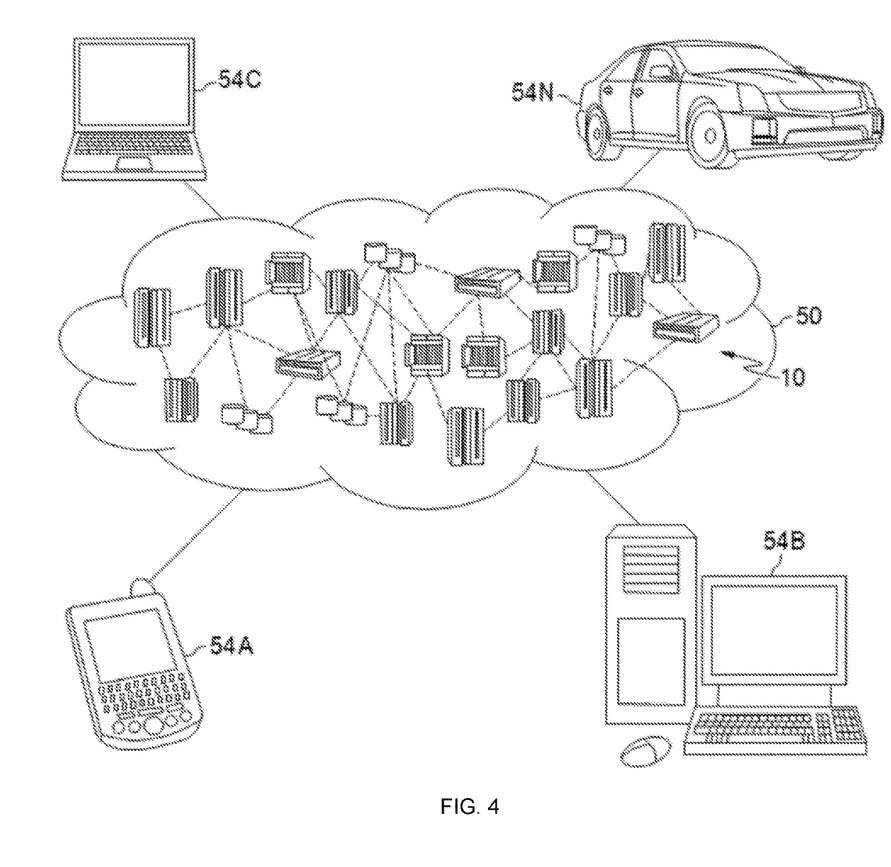
FIG. 4 depicts a cloud computing environment according to an embodiment of the present invention.

Referring now to FIG. 4, illustrative cloud computing environment 50 is depicted. As shown, cloud computing environment 50 includes one or more cloud computing nodes 10 with which local computing devices used by cloud consumers, such as, for example, personal digital assistant (PDA) or cellular telephone 54A, desktop computer 54B, laptop computer 54C, and/or automobile computer system 54N may communicate. Nodes 10 may communicate with one another. They may be grouped (not shown) physically or virtually, in one or more networks, such as Private, Community, Public, or Hybrid clouds as described hereinabove, or a combination thereof. This allows cloud computing environment 50 to offer infrastructure, platforms and/or software as services for which a cloud consumer does not need to maintain resources on a local computing device. It is understood that the types of computing devices 54A-N shown in FIG. 4 are intended to be illustrative only and that computing nodes 10 and cloud computing environment 50 can communicate with any type of computerized device over any type of network and/or network addressable connection (e.g., using a web browser).

Figure 5:
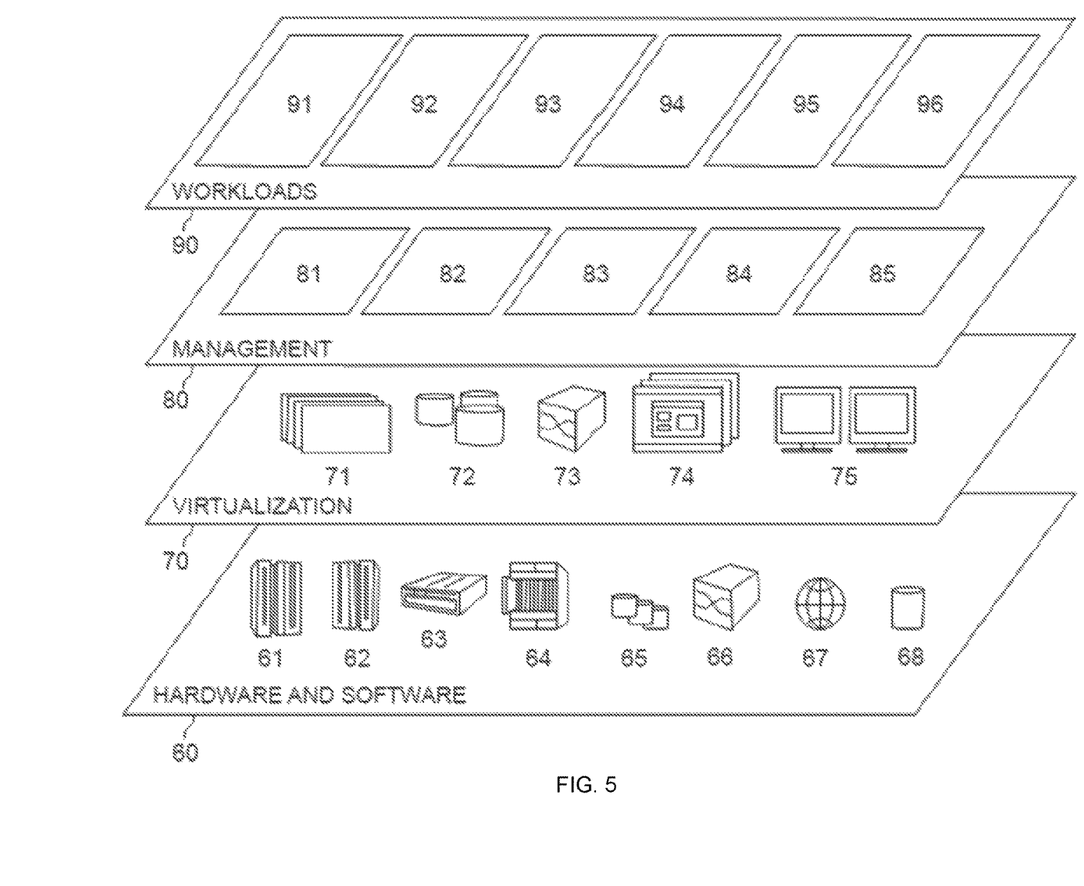
FIG. 5 depicts abstraction model layers according to an embodiment of the present invention.

Referring now to FIG. 5, a set of functional abstraction layers provided by cloud computing environment 50 (FIG. 4) is shown. It should be understood in advance that the components, layers, and functions shown in FIG. 5 are intended to be illustrative only and embodiments of the invention are not limited thereto. As depicted, the following layers and corresponding functions are provided:

Hardware and software layer 60 includes hardware and software components. Examples of hardware components include: mainframes 61; RISC (Reduced Instruction Set Computer) architecture based servers 62; servers 63; blade servers 64; storage devices 65; and networks and networking components 66. In some embodiments, software components include network application server software 67 and database software 68.

Virtualization layer 70 provides an abstraction layer from which the following examples of virtual entities may be provided: virtual servers 71; virtual storage 72; virtual networks 73, including virtual private networks; virtual applications and operating systems 74; and virtual clients 75.

In one example, management layer 80 may provide the functions described below. Resource provisioning 81 provides dynamic procurement of computing resources and other resources that are utilized to perform tasks within the cloud computing environment. Metering and Pricing 82 provide cost tracking as resources are utilized within the cloud computing environment, and billing or invoicing for consumption of these resources. In one example, these resources may include application software licenses. Security provides identity verification for cloud consumers and tasks, as well as protection for data and other resources. User portal 83 provides access to the cloud computing environment for consumers and system administrators. Service level management 84 provides cloud computing resource allocation and management such that required service levels are met. Service Level Agreement (SLA) planning and fulfillment 85 provide pre-arrangement for, and procurement of, cloud computing resources for which a future requirement is anticipated in accordance with an SLA.

Workloads layer 90 provides examples of functionality for which the cloud computing environment may be utilized. Examples of workloads and functions which may be provided from this layer include: mapping and navigation 91; software development and lifecycle management 92; virtual classroom education delivery 93; data analytics processing 94; transaction processing 95; and bias of physical controllers in mechanical systems 96.

The terminology used herein is for the purpose of describing particular embodiments only and is not intended to be limiting of the invention. As used herein, the singular forms "a", "an" and "the" are intended to include the plural forms as well, unless the context clearly indicates otherwise. It will be further understood that the root terms "include" and/or "have", when used in this specification, specify the presence of stated features, integers, steps, operations, elements, and/or components, but do not preclude the presence or addition of at least one other feature, integer, step, operation, element, component, and/or groups thereof.

The corresponding structures, materials, acts, and equivalents of all means plus function elements in the claims below are intended to include any structure, or material, for performing the function in combination with other claimed elements as specifically claimed. The description of the present invention has been presented for purposes of illustration and description, but is not intended to be exhaustive or limited to the invention in the form disclosed. Many modifications and variations will be apparent to those of ordinary skill in the art without departing from the scope and spirit of the invention. The embodiment was chosen and described in order to best explain the principles of the invention and the practical application, and to enable others of ordinary skill in the art to understand the invention for various embodiments with various modifications as are suited to the particular use contemplated.

What is claimed is:

1. A method to control a mechanical system based on the cognitive state of at least one user, said method comprising:
performing a first action at an input device, wherein the input device is associated with at least one user;
detecting the cognitive state of the at least one user at the input device by a first processing unit;
determining a change to the first action based on the cognitive state of the at least one user by a second processing unit; and
performing a controlled action by a controller based on the recommended change, the controlled action selected from the group consisting of delaying a command from the at least one user, sending an alert to a third party indicating the detected cognitive state of the at least one user, providing a recommendation to the at least one user, and activation of a detent in the physical controller.

2. The method according to claim 1, wherein the cognitive state of the at least one user is selected from the group consisting of above a threshold level of anxiety, above a threshold level of level of elation, above a threshold level hesitation, above a threshold level of distraction, above a threshold level of fatigue, above a threshold level of frustration, above a threshold level of nervousness, above a threshold level of panic, above a threshold level of anger, below a threshold level of expertise, and a disease cognitive state.

3. The method according to claim 1, wherein the cognitive state of the at least one user includes above a threshold level of anxiety, above a threshold level of level of elation, above a threshold level hesitation, above a threshold level of distraction, above a threshold level of fatigue, above a threshold level of frustration, above a threshold level of nervousness, above a threshold level of panic, above a threshold level of anger, below a threshold level of expertise, and a disease cognitive state.

4. The method according to claim 1, wherein said controlled action includes activating an autopilot system in the mechanical system when the processor determines that the cognitive state of the at least one user is selected from the group consisting of above a threshold level of anxiety, above a threshold level of elation, above a threshold level of hesitation, above a threshold level of distraction, above a threshold level of fatigue, above a threshold level of frustration, above a threshold level of nervousness, above a threshold level of panic, above a threshold level of anger, below a threshold level of expertise, and a neurological disease cognitive state.

5. The method according to claim 1, wherein said controlled action is performed when the processor determines that the cognitive state of the at least one user is selected from the group consisting of above a threshold level of anxiety, above a threshold level of elation, above a threshold level of hesitation, above a threshold level of distraction, above a threshold level of fatigue, above a threshold level of frustration, above a threshold level of nervousness, above a threshold level of panic, above a threshold level of anger, below a threshold level of expertise, and a neurological disease cognitive state.

6. The method according to claim 1, wherein said controlled action is performed when the processor determines that the cognitive state of the at least one user is above a threshold level of anxiety, above a threshold level of elation, above a threshold level of hesitation, above a threshold level of distraction, above a threshold level of fatigue, above a threshold level of frustration, above a threshold level of nervousness, above a threshold level of panic, above a threshold level of anger, below a threshold level of expertise, and a neurological disease cognitive state.

7. The method according to claim 1, wherein said controlled action includes increasing a sensitivity of a physical controller of the mechanical system when the processor determines that the cognitive state of the at least one user is selected from the group consisting of above a threshold level of anxiety, above a threshold level of elation, above a threshold level of hesitation, above a threshold level of distraction, above a threshold level of fatigue, above a threshold level of frustration, above a threshold level of nervousness, above a threshold level of panic, above a threshold level of anger, below a threshold level of expertise, and a neurological disease cognitive state.

8. The method according to claim 1, wherein said controlled action includes decreasing a sensitivity of a physical controller of the mechanical system when the processor determines that the cognitive state of the at least one user is selected from the group consisting of above a threshold level of anxiety, above a threshold level of elation, above a threshold level of hesitation, above a threshold level of distraction, above a threshold level of fatigue, above a threshold level of frustration, above a threshold level of nervousness, above a threshold level of panic, above a threshold level of anger, below a threshold level of expertise, and a neurological disease cognitive state.

9. The method according to claim 1, wherein said controlled includes changing a type of vibration feedback in the physical controller of the mechanical system when the processor determines that the cognitive state of the at least one user is selected from the group consisting of above a threshold level of anxiety, above a threshold level of elation, above a threshold level of hesitation, above a threshold level of distraction, above a threshold level of fatigue, above a threshold level of frustration, above a threshold level of nervousness, above a threshold level of panic, above a threshold level of anger, below a threshold level of expertise, and a neurological disease cognitive state.

10. The method according to claim 1, wherein said controlled action is selected from the group consisting of decreasing an amount of vibration feedback and changing a type of vibration feedback in the physical controller of the mechanical system when the processor determines that the cognitive state of the at least one user is selected from the group consisting of above a threshold level of anxiety, above a threshold level of elation, above a threshold level of hesitation, above a threshold level of distraction, above a threshold level of fatigue, above a threshold level of frustration, above a threshold level of nervousness, above a threshold level of panic, above a threshold level of anger, below a threshold level of expertise, and a neurological disease cognitive state.

11. The method according to claim 1, wherein said detecting of the cognitive state of the at least one user includes detecting a level of fatigue of the at least one user based on a factor selected from the group consisting of a calendar of the at least one user, a facial expression of the at least one user, and head nods detected by the input device.

12. The method according to claim 1, wherein the mechanical system includes an automobile, the input device includes a camera on the automobile, and wherein said detecting of the cognitive state of the at least one user includes detecting that the at least one user is at least one of distracted and fatigued when lane deviation is detected in the input.

13. The method according to claim 1, wherein said detecting of the cognitive state of the at least one user includes detecting a level of hesitation of the at least one user by a timing analysis, said timing analysis including:
  determining an average response time for a task by the at least one user;
  determining a current response time for the task by the at least one user;
  determining that the at least one user has a high level of hesitation when the current response time for the task by the at least one user exceeds the average response time for a task by the at least one user by a threshold amount of time.

14. The method according to claim 1, wherein said detecting of the cognitive state of the at least one user includes detecting a level of anxiety of the at least one user by detecting hand tremors of the at least one user with a sensor in a physical controller of the mechanical system.

15. The method according to claim 1, wherein said detecting of the cognitive state of the at least one user includes detecting the cognitive state of the at least one user from information from a calendar of the at least one user and a profile of the at least one user, the profile of the at least one user including a level of expertise of the at least one user, a disease cognitive state of the at least one user, and a list of medications of the at least one user.

16. A system to control a mechanical system based on the cognitive state of a user, said system comprising:
  an input device associated with at least one user, wherein a first action is performed at said input device;
  a processor connected to said input device, said processor detects the cognitive state of the at least one user at said input device and determines a change to a first action based on the cognitive state of the user; and
  a controller connected to said processor, said controller performs a controlled action based on the recommended change, the controlled action selected from the group consisting of delaying a command from the at least one user, sending an alert to a third party indicating the detected cognitive state of the at least one user, providing a recommendation to the at least one user, and activation of a detent in the input device.

17. The system according to claim 16, wherein said processor detects the cognitive state of the at least one user from a factor selected from the group consisting of a facial expression of the at least one user, information from a calendar of the at least one user, a profile of the at least one user, and analysis of audible input, the analysis of audible input including detected keywords, tone of spoken words, frequency of the spoken words, and pitch of the spoken words.

18. An input device associated with at least one user, said input device comprising:
  a user interface, wherein a first action is performed at said user interface;
  a first processing unit connected to said user interface, said first processing unit detects the cognitive state of the at least one user at said user interface; and
  a second processing unit connected to said first processing unit, said second processing unit determines a change to a first action based on the cognitive state of the user, the change to the first action selected from the group consisting of delaying a command from the at least one user, sending an alert to a third party indicating the detected cognitive state of the at least one user, providing a recommendation to the at least one user, and activation of a detent in the user interface.

* * * * *